United States Patent [19]

Siepser et al.

[11] Patent Number: 5,147,394
[45] Date of Patent: Sep. 15, 1992

[54] HIGH REFRACTIVE INDEX POLYMERIC COMPOSITIONS SUITABLE FOR USE AS EXPANSILE HYDROGEL INTRAOCULAR LENSES

[76] Inventors: Steven B. Siepser, 866 Downgintown Pike, West Chester, Pa. 19380; B. David Halpern, R.D. #4 1057 Kingsley Rd., Jenkintown, Pa. 19046; Wolf Karo, 328 Rockledge Ave., Huntingdon Valley, Pa. 19006

[21] Appl. No.: 615,440

[22] Filed: Nov. 16, 1990

Related U.S. Application Data

[63] Continuation of Ser. No. 455,087, Dec. 22, 1989, abandoned, which is a continuation of Ser. No. 107,281, Oct. 9, 1987, abandoned.

[51] Int. Cl.$^5$ ................................................ A61F 2/16
[52] U.S. Cl. .......................................... 623/6; 623/66; 351/160 H; 523/106; 523/108; 524/548; 526/264
[58] Field of Search ................. 623/6, 66; 351/160 H; 423/206, 108; 524/548; 526/264

[56] References Cited

U.S. PATENT DOCUMENTS

| | | | |
|---|---|---|---|
| 4,036,788 | 7/1977 | Steckler | 528/391 |
| 4,123,408 | 10/1978 | Gordon | 351/160 H |
| 4,430,458 | 2/1984 | Tighe et al. | 351/160 H |
| 4,556,998 | 10/1985 | Siepser | 623/6 |
| 4,608,049 | 8/1986 | Kelman | 623/6 |
| 4,693,939 | 9/1987 | Ofstead | 351/160 H |
| 4,849,285 | 7/1989 | Dillon | 623/13 |
| 5,092,884 | 3/1992 | Devereux et al. | 623/11 |

OTHER PUBLICATIONS

Morrison, R. J., "Hydrophilic Contact Lenses", Journal of Amer. Optometric Sov., vol. 37, No. 3, Mar. 1966, pp. 211–218.

*Primary Examiner*—Randall L. Green
*Assistant Examiner*—Paul Prebilic
*Attorney, Agent, or Firm*—Eugene E. Renz, Jr.

[57] ABSTRACT

Flexible, crosslinked polymeric compositions providing transparent hydrogels having a refractive index in the dehydrated (dry) state of at least about 1.53 and having equilibrium water content of at least 40% by weight of the polymeric gel for use an expansile intraocular lenses for surgical implantation. The dehydrated polymeric compositions are capable of hydration by natural fluids present in the eye to expand about 180% after implantation and in the fully swollen state have refractive indices of at least 1.40. They are prepared by polymerizing a multicomponent monomeric mixture consisting essentially of from about 50 to 75% by weight vinyl pyrrolidone, from about 3.25 to 12.5% by weight of 2-hydroxypropyl acrylate, from about 3.25 to 12.5% by weight of 2-hydroxyethyl methacrylate, from about 5 to 35% by weight of acrylamide and as a fifth component a crosslinking agent in an amount of from 1.25 to 15 parts per hundred parts of monomers by weight selected from the group consisting of tetraethylene glycol dimethacrylate and dibromoneopentyl glycol dimethacrylate.

5 Claims, No Drawings

HIGH REFRACTIVE INDEX POLYMERIC COMPOSITIONS SUITABLE FOR USE AS EXPANSILE HYDROGEL INTRAOCULAR LENSES

This is a Continuation-in-Part of my copending application entitled HIGH REFRACTIVE INDEX POLYMERIC COMPOSITIONS SUITABLE FOR USE AS EXPANSILE HYDROGEL INTRAOCULAR LENSES filed Dec. 22, 1989, Ser. No. 07/455,087 now abandoned, which in turn is a Continuation of my prior application entitled HIGH REFRACTIVE INDEX POLYMERIC COMPOSITIONS SUITABLE FOR USE AS EXPANSILE HYDROGEL INTRAOCULAR LENSES, filed Oct.9, 1987, Ser. No. 07/107,281 now abandoned.

FIELD OF THE INVENTION

This invention relates to improved expansile hydrogel intraocular lenses suitable for small incision cataract surgery and their preparation from certain chemicals. More specifically, this invention relates to flexible, biocompatible, optically clear, castable, moldable or machinable hydrogels having refractive indices in the dehydrated state of at least 1.53 and at least 1.40 in a swollen state.

BACKGROUND OF THE INVENTION

Cataract surgery is among the most common major surgical procedures performed in the United States today. In fact, it is the most common surgical procedure performed in Medicare beneficiaries who are 65 years or older. With steadily increasing frequency in appropriately selected patients, cataract surgery is combined with intraocular lens implantation. While much work has been done since the first intraocular lens was implanted in the human eyes in 1949, there remains a substantial need for an improved expansile hydrogel intraocular lens which will enhance the safety and efficiency of cataract surgery.

This need is fully described in U.S. Pat. No. 4,556,998, issued Dec. 10, 1985 in the name of Steven B. Siepser and entitled ARTIFICIAL INTRAOCULAR LENSES AND METHOD FOR THEIR SURGICAL IMPLANTATION. The entire disclosure of this Siepser Patent is hereby being incorporated herein by reference.

The presently used materials, i.e. copolymers of 2-hydroxyethyl methacrylate with vinyl pyrrolidone or ethylenedimethacrylate with their sufficient 170% swell characteristics, have refractive indices that are too low when fully hydrated. It seems that the ideal highest power small incision lens that can be made with the most modern technology is about 21 diopters. Even such an advanced lens would exclude a considerable portion of the "cataract" market.

It is well known that the refractive index of lens material affect the base curves, diameter, edge and certain thickness relative to any fixed dioptic power. For example, the optical properties of high refractive index glass permit use of a relatively shallow base curve, thus avoiding excess edge thickness in glasses for patients with extreme myopia. In preparing and designing an expansile hydrogel intraocular lens one must keep in mind that the refractive index of all hydrogels usually decrease in linear proportion to the amount of hydration. In these applications maximum expansion is needed, i.e. the higher the expansion, the higher the water uptake. Inherently, the expansion ratio of a material is limited by the water uptake which reduces its refractive power beyond acceptable limits.

The refractive (diopter) power of a lens is a function of its refractive index and the radii of curvature of its optical surfaces. To obtain a lens of given power with a reduced refractive index, the lens designer must use a smaller radius, i.e. tighter curve, for one or both optical surfaces. For a given diameter lens, this will result in a lens that is thicker along the optical axis. Because of the relatively low refractive indices of most conventional hydrogels, a larger cross sectional diameter at the equator are called for. This increase is not conducive to small incision cataract surgery.

As has been pointed out in U.S. Pat. No. 4,556,998, hydrophilic (hydrogel) intraocular lenses offer many advantages compared to present hydrophobic lenses as typified by poly (methyl methacrylate) and polypropylene. Not only does the use of hydrogels permit smaller incision cataract surgery with resultant decrease in wound healing time, but it also protects the corneal endothelium and leads to less mechanical and immunologic intraocular inflammation. Nevertheless, widespread use of hydrogel compositions as expansile intraocular lenses to date continues to be limited by the unavailability of materials which are biologically and chemically inert, flexible, displaying refractive indices above 1.40 in the swollen state, and at least 1.53 in the dehydrated state and capable of fabrication to desired forms.

To obtain corrective powers much greater than 25D with a 6 mm optic, researchers have found that hydrated polymers, i.e. polymeric hydrogels, must have refractive indices of at least 1.40 because the refractive index of the hydrogel lens is reduced by loss of the air/lens interface and the hydrated lens' high water content. To obtain this high a refractive index in the fully swollen state, it is necessary that the polymers in their dry state (prior to hydration) have a refractive index of at least 1.525 (1.53). None of the commercially available expansile intraocular lenses possess this level of refractive index today. Nor has there been any appreciation to date of just how critical each fractional increase in refractive index is in expansile concept intraocular lens.

In previous technology involved in the development of hydrogels the refractive index of the material was not important. These materials were most often used in refractive use as a contact lens and the refractive index of air being 1.0 and in water 1.33, the difference between water and the lens being less than 0.1 was not really significant. In current application these lenses are placed in the eye thereby making their refractive index far more critical. The refractive index of the media inside the eye is 1.33 and any increase in the hundredths in refractive indexes results in a very significant decrease in the thickness and contours of the lens needed to refract the light.

The importance of every hundredths of increase in refractive index can not be overemphasized for each hundredth results in a significant decrease in the thickness of the lens. In small incisions cataract surgery there is a need for surgeons to reduce the size of the opening in the eye to do cataract surgery. The importance of this is that intraocular lenses must be designed so that they are quite small and can fit through these smaller openings. The technology presently available is in silicone and several patents have been issued on silicones that have increased refractive indexes. The importance there is it decreases the thickness of the lens and allows them to be folded and passed through smaller openings. In the *Expansile Concept Intraocular Lens* this is even far more critical. In fact every 1/100 increase in refractive index results in a 5% decrease in the center thickness of a lens needed of similar power. This is an extremely significant amount and represents new technical grounds.

It is apparent from the foregoing discussion that while much work has been and is being done in the hydrogel art, there has been no recognition of the significance of small incremented increases in refractive index in the field of expansile intraocular lens.

It is a primary object of the present invention to provide a polymeric hydrogel which is flexible, optically clear, possessing a dry refractive index of at least 1.53 and in a swollen state a refractive index of at least 1.40 and capable of being machined or formed in the dry state into an intraocular lens.

It is another object of the invention to provide a crosslinked polymer composition in transparent gel form having an equilibrium water content of at least 40% by weight based on the weight of the polymeric gel for use in an expansile intraocular lens.

In the preparation of the new lenses, the hydrogel polymer in its dry, hardened state is formed into rods which are cut into discs. These discs are cut into various shapes and then milled into desired shapes for implantation. The dioptic power is ground into the optic. These lens are then tumble polished to provide a smooth surface finish and remove rough edges. The size or depth of the eye and the curves of the front of the eye are measured and determined for each individual patient by the physician by standard examination and calculation. The lenses may also be made by spin casting, molding, or any other suitable method.

SUMMARY OF THE INVENTION

The foregoing and other objects of the invention which will become apparent below are achieved by polymerizing certain monomers present in specialized quantities in the mixture to produce polymeric hydrogels which can be fabricated into expansile intraocular lenses which are bicompatible, swellable, optically clear, flexible, self-supporting and self-aligning on the optical axis, and possess refractive indices above 1.40 in the hydrated sates and at or above 1.53 in the dehydrated state. The hydrogels of the invention can be inserted in their dehydrated or "xerogel" state through incisions of less than 3.5 mm and can then be expanded up to about 180% to a 5.8 mm optic in a matter of 20 or so minutes.

DETAILED DESCRIPTION OF THE PREFERRED EMBODIMENT

Monomer compositions which were polymerized in polymerization cells to produce the polymers of this invention included 1-vinyl-2-pyrrolidone, hydroxypropyl acrylate, 2-hydroxyethyl methacrylate, acrylamide, dibromoneopentyl glycol dimethacrylate and tetraethylene glycol dimethacrylate. Each cell consisted of two microscope slides separated by an elastomeric spacer and held together with spring clamps. The inside of each cell was coated with lecithin as a "parting" agent prior to use.

To the appropriate monomer solutions there was added 0.05 g of a, a'- azobisisobutylonitrile per 20 ml of monomer mixture. These compositions were placed in the polymerization cells and heated at 60° C., usually overnight. In some experiments, the initiator concentration was reduced to 0.0025 g per 10 ml of monomer to reduce the formation of bubbles in the polymers. The preferred catalytic initiator is hydrogen peroxide. Benzoyl peroxide is also operative.

Refractive indices of the liquid monomer compositions were taken with an Abbe refractometer at 20° using the D line of sodium. The refractive indices of the resultant polymers were also taken on the Abbe refractometer by adhering the polymer to the measuring prism of the instrument with highly refractive 1-bromonaphthalene and measuring the index in reflected light.

The swelling of the polymers was determined by first measuring the length and width of a polymer sample. The polymers were then immersed in distilled water and their dimensions again measured after 14 days. It is recognized that since the aqueous humor in the eye has a different osmotic pressure than pure water this test gives merely a first approximation.

The results of the polymerizations using 1-vinyl-2-pyrrolidone as the major component are summarized in Table 1.

TABLE 1

| Example Number | 1 | 2 | 3 | 4 |
|---|---|---|---|---|
| Monomers | | | | |
| Vinyl pyrrolidone (VP) | 66.67% | 58.33 | 58.33 | 58.33 |
| Acrylamide (AA) | 20.00 | 25.00 | 25.00 | 25.00 |
| 2-hydroxypropyl acrylate (HPA) | 6.67 | 8.33 | 8.33 | 8.33 |
| 2-hydroxyethyl methacrylate (HEMA) | 6.67 | 8.33 | 8.33 | 8.33 |
| Crosslinking Agent (parts per hundred) | | | | |
| Dibromoneopentyl glycol dimethacrylate (DMGDMA) | 8.33 | — | 4.17 | 1.67 |
| Tetraethylene glycol dimethacrylate (TEGDMA) | — | 2.05 | — | — |
| $n_D^{20}$ (dry polymer) | 1.553 | 1.520 | 1.557 | 1.531 |

On polymerization, the refractive indices of the copolymers were higher than those of the monomer mixture from which they were formed.

It is to be understood that the compositional limits of the hydrogels of this invention can vary as follows: vinyl pyrrolidone from about 50 to 75% by weight, acrylamide about 5 to 35% by weight, hydroxypropyl acrylate from about 3.25 to 12.5% by weight and hydroxyethyl methacrylate from about 3.25 to 12.5% by weight. It being further understood that the total of the percentages of the above-named monomeric components in the polymeric compositions of the invention equals 100. To 100 parts of the above monomeric mixed compositions, there is added a crosslinking agent and catalytic initiator in concentrations which can vary from about 1.25 to 15 parts per hundred. The hydrogels have an equilibrium water content of at least 40% by weight of the gel.

The preferred crosslinking agents are dibromoneopentyl glycol dimethacrylate and tetraethylene glycol dimethacrylate. Other crosslinking agents which can be used include polyethylene glycol 600 dimethacrylate, polyethylene glycol 400 dimethacrylate, trimethylene glycol dimethacrylate, ethylene glycol dimethacrylate, glycerol triethoxy triacrylate, and glycerol trimethacrylate.

Even though particular embodiments of the invention have been illustrated and described herein, i.e. Examples 1 through 4, it is not intended to limit the invention and modifications may be made therein within the scope of the claims presented.

What is claimed is:

1. A high refractive index polymeric composition which consists essentially of polymerized mixture of four monomeric components and a crosslinking agent, said mixture consisting essentially of from about 50 to 75% by weight of 2-vinyl pyrrolidone, from about 3.25 to 12.5% by weight of 2-hydroxypropyl acrylate, from about 5 to 35% by weight of acrylamide, from about 3.25 to 12.5% by weight 2-hydroxyethyl methacrylate, and from about 1.25 to 15 parts per hundred parts of said polymerized mixture by weight of a crosslinking agent selected from the group consisting of tetraethylene glycol dimethacrylate and dibromoneopentyl glycol dimethacrylate, the monomeric components totaling 100% by weight exclusive of the crosslinking agent.

2. An expansile, polymeric, optically clear hydrogel having a dehydrated state, wherein said hydrogel is capable of being formed in the dehydrated state into an intraocular lens and having
   (a) an equilibrium water content of at least 40 per cent by weight of the gel,
   (b) a refractive index measured from air with respect to the lens material of at least 1.53 in the dehydrated state and at least 1.40 in a swollen state, and
   (c) a swell factor in aqueous humor which renders the intraocular lens particularly suitable for small incision cataract surgery.

3. The hydrogel of claim 2, wherein the swell factor of the hydrogel is about 180%.

4. The hydrogel of claim 3, wherein the hydrogel is sized to be inserted in its dehydrated state through an incision of less than 3.5 mm and expanded by the aqueous humor to a 5.8 mm optic in about twenty minutes.

5. A process for preparing a hydrogel of claim 1 which comprises polymerizing in the presence of catalytic initiator selected from the group consisting of benzoyl peroxide and hydrogen peroxide a monomeric mixture comprising 2-vinyl pyrrolidone, acrylamide, 2-hydroxypropyl acrylate, 2-hydroxethyl methacrylate and an additive selected form the group consisting of tetraethylene glycol dimethacrylate and dibromoneopentyl glycol dimethacrylate.

* * * * *